United States Patent [19]

Worthen et al.

[11] Patent Number: 5,445,164

[45] Date of Patent: Aug. 29, 1995

[54] CERVICAL TISSUE SAMPLING DEVICE

[75] Inventors: W. G. Worthen, Springdale, Ark.; Howard V. Worthen, deceased, late of Oklahoma City, Okla., by Mildred W. Worthen, administrator; W. J. Dunn, Fayetteville, Ark.

[73] Assignee: Gynetech, Inc., Fayetteville, Ark.

[21] Appl. No.: 60,414

[22] Filed: May 11, 1993

[51] Int. Cl.⁶ .............................. A61B 5/00
[52] U.S. Cl. .................................... 128/759
[58] Field of Search ............... 128/749, 756–759; 604/1, 14–16

[56] References Cited

U.S. PATENT DOCUMENTS

| 16,680 | 2/1857 | Russell | 604/15 |
|---|---|---|---|
| 545,102 | 8/1895 | Sleem | 604/15 |
| 1,794,221 | 2/1931 | Washburn et al. | 604/15 |
| 2,847,000 | 8/1958 | Nieburgs | 604/16 |
| 3,626,470 | 12/1971 | Antonides | 128/759 |
| 3,881,464 | 5/1975 | Levene . | |
| 4,157,709 | 6/1979 | Schuster et al. | 604/14 |
| 4,227,537 | 10/1980 | Suciu et al. | 128/756 |
| 4,628,941 | 12/1986 | Kosasky | 128/759 |
| 4,784,158 | 11/1988 | Okimoto | 128/771 |
| 4,877,037 | 10/1989 | Ko et al. | 128/756 |
| 4,946,440 | 8/1990 | Hall | 604/95 |
| 5,279,307 | 1/1994 | Mohajer | 128/757 |

FOREIGN PATENT DOCUMENTS 2329443 1/1974 Germany .

*Primary Examiner*—Max Hindenburg
*Attorney, Agent, or Firm*—Boyd D. Cox

[57] ABSTRACT

A cervical tissue sampling device to allow women to collect tissue samples at home for transmission to a laboratory by mail or other means includes a cylindrical barrel having an open circular front end and an open circular rear end terminating in a radially extending irregularly shaped finger grip flange. A plunger assembly slidably received within the barrel includes a circular brush and surrounding circular sponge for collecting cervical tissue and mucous. The brush and sponge collection assembly is detachably secured to the plunger shaft by a quick release connection. In use, the barrel is inserted by a female into her vagina with the sponge and brush disposed in a retracted condition within the barrel 12. After insertion, the plunger is moved to an extended condition and rotated to collect tissue and mucous samples on the brush and sponge. After the samples have been collected, the sponge and brush are detached from the plunger shaft and mailed in a sealed container to a laboratory for analysis.

40 Claims, 4 Drawing Sheets

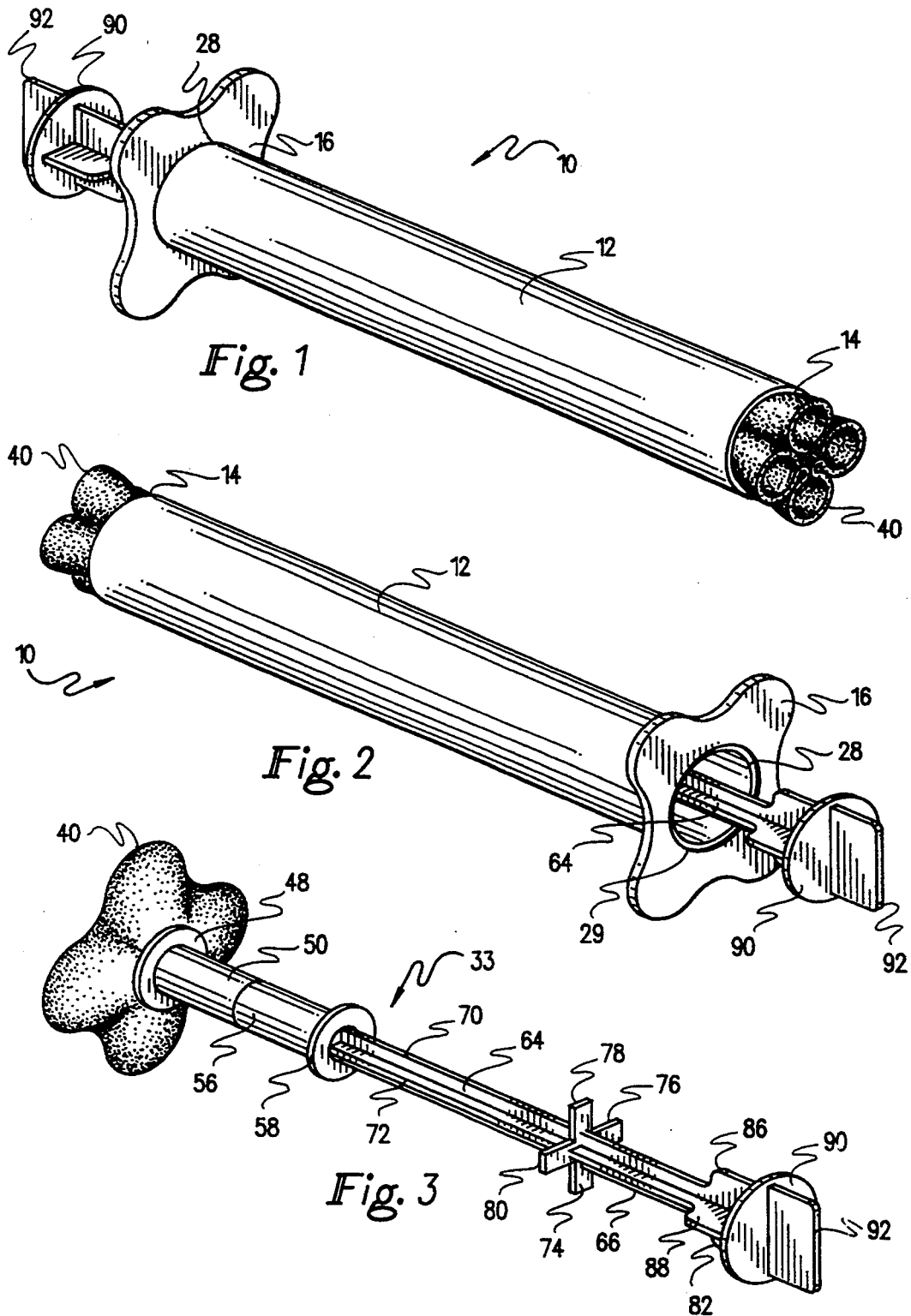

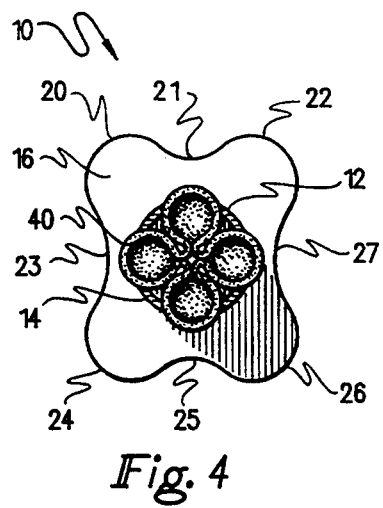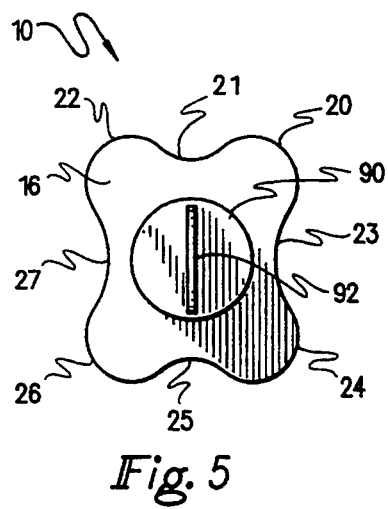
Fig. 4        Fig. 5
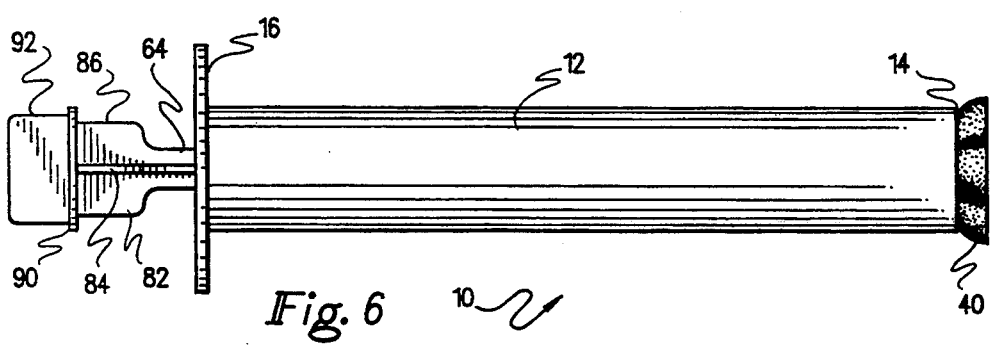
Fig. 6
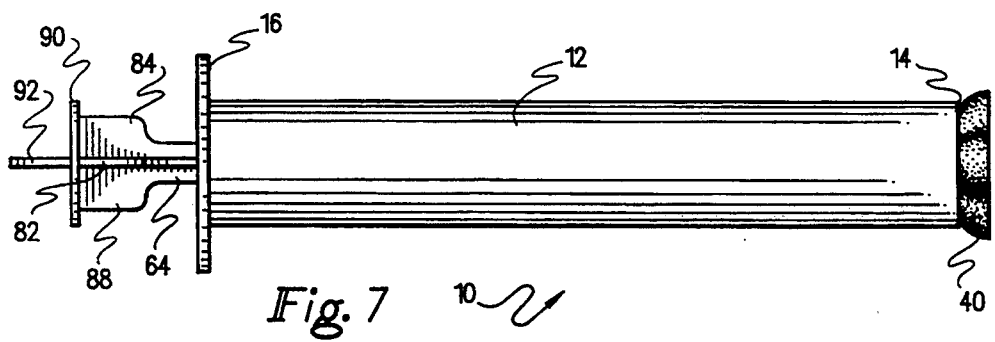
Fig. 7

CERVICAL TISSUE SAMPLING DEVICE

BACKGROUND OF THE INVENTION

Microscopic screening of slides of sampled cervical tissue and mucous has proven to be a highly effective method of reducing the mortality rate of women from cervical cancer. The American Cancer Society recommends that women obtain the so-called Pap-Smear test not less than annually. Unfortunately, many women do not participate in annual screening for a variety of reasons, including the personally invasive nature of the procedure, the high cost of an office visit to a gynecologist, distrust of the accuracy of the test, and time lost from work or other activities to visit a physician's office to be tested. Studies indicate that effective annual screening should reduce the incidence and mortality of invasive cervical cancer by ninety percent.

SUMMARY OF THE INVENTION

In order to address these concerns, the present invention provides a cervical tissue sampling device which allows females to obtain in the privacy of the individual's home a viable specimen including endocervical, cervical, and vaginal cavity cells for laboratory testing.

In order to achieve these and other objects of the invention, the present invention provides an improved cervical tissue sampling device which allows women to collect tissue samples at home for transmission to a laboratory by mail or other means and includes a cylindrical barrel having an open circular front end and an open circular rear end terminating in a radially extending irregularly shaped finger grip flange. A plunger assembly slidably received within the barrel includes a circular brush and surrounding circular sponge for collecting cervical tissue and mucous. The brush and sponge collection assembly is detachably secured to the plunger shaft by a quick release connection. In use, the barrel is inserted by a female into her vagina with the sponge and brush disposed in a retracted condition within the barrel 12. After insertion, the plunger is moved to an extended condition and rotated to collect tissue and mucous samples on the brush and sponge. After the samples have been collected, the sponge and brush are detached from the plunger shaft and mailed in a sealed container to a laboratory for analysis.

These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

FIG. 1 is a front perspective view illustrating the cervical tissue sampling device of the present invention in an assembled, retracted condition.

FIG. 2 is a rear perspective view illustrating the cervical tissue sampling device of the present invention in an assembled, retracted condition.

FIG. 3 is a rear perspective view illustrating the plunger assembly of the cervical tissue sampling device of the present invention.

FIG. 4 is a front end elevational view illustrating the cervical tissue sampling device of the present invention in a retracted condition.

FIG. 5 is a rear end elevational view illustrating the cervical tissue sampling device of the present invention.

FIG. 6 is a side elevational view illustrating the cervical tissue sampling device of the present invention in a retracted condition.

FIG. 7 is a top plan view illustrating the cervical tissue sampling device of the present invention in a retracted condition.

DETAILED DESCRIPTION OF THE PREFERRED EMBODIMENT

Figure 8:
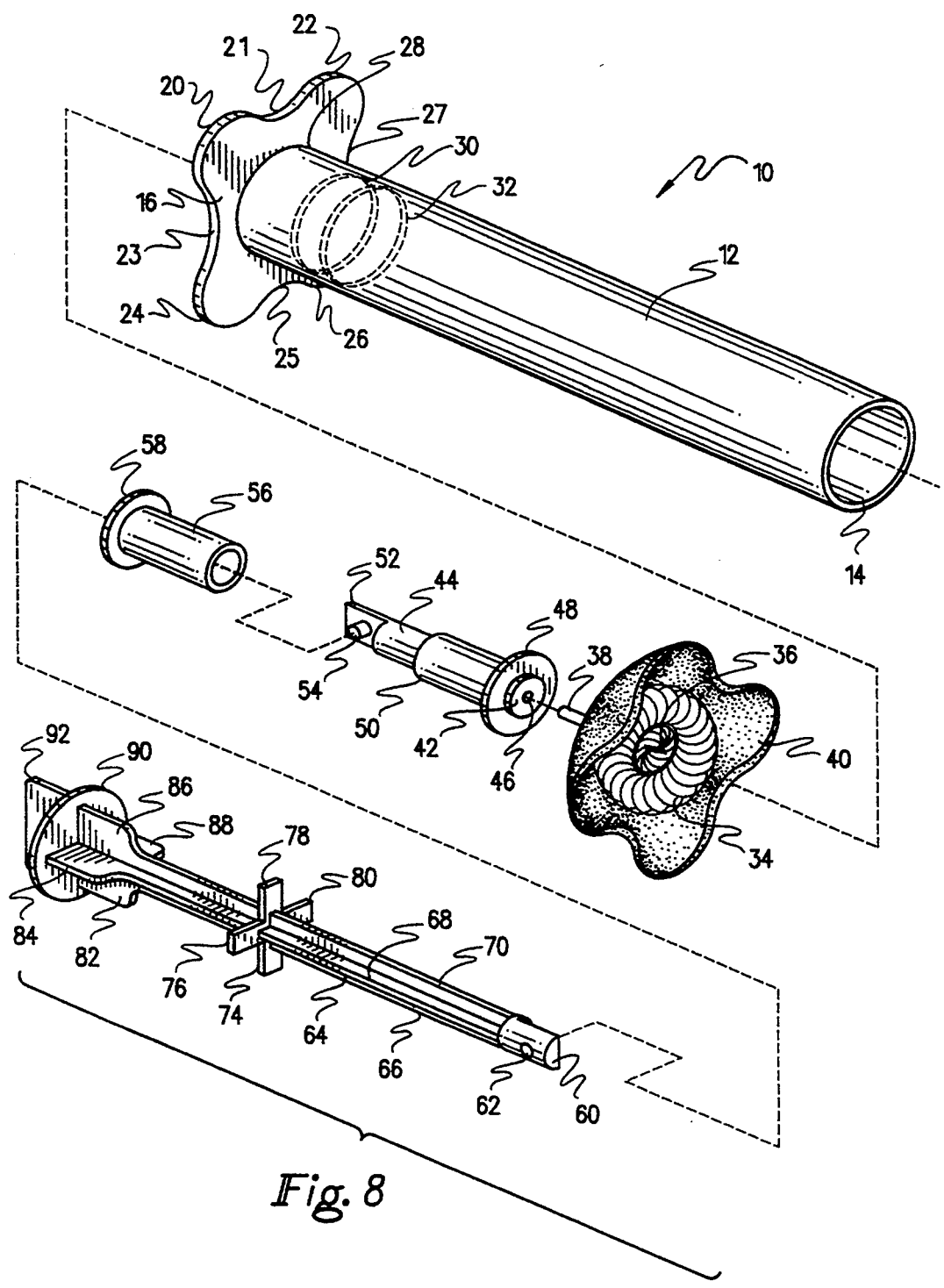
FIG. 8 is an exploded perspective view illustrating the component parts of the cervical tissue sampling device of the present invention.

Referring now to the drawings, wherein like reference numerals designate corresponding structure throughout the views, and referring in particular to FIGS. 1, 2, and 8, the cervical tissue sampling device 10 according to a first preferred embodiment of the invention includes an elongated substantially rigid, substantially cylindrical barrel 12 possessing a circular open front end 14 and terminating at a rear open circular end 28 within a circular recess 29 in an irregularly shaped radially extending finger grip flange 16. The barrel 12 and flange 16 are preferably formed from #PE2067 low-density polyethylene, available from Branchcomb Industries, Sapulpa, Ok. As shown in FIGS. 4, 5, and 8, the finger grip flange 16 possesses convex arcuately curved corner projecting portions 20, 22, 24, and 26 spaced around the periphery of the flange 16. These corner projections are separated by respective concave arcuate recesses 21, 23, 25, and 27. As may be appreciated with reference to FIG. 2, the barrel 12 may be integrally molded with the flange 16, or alternatively may be assembled from separate components by press fitting the rear circular open end 28 of the barrel 12 into a conforming aperture formed centrally in the flange 16. Suitable adhesives may also be employed to effect securement of the flange 16 to the barrel 12. The barrel 12, as depicted in FIG. 8, possesses internal axially spaced annular ridges 30 and 32 formed internally within the barrel 12 adjacent flange 16 for the purpose of retaining a plunger assembly therein, in a manner to be described subsequently in greater detail.

With reference to FIGS. 3 and 8, the cervical tissue sampling device 10 according to the present invention includes a plunger assembly 33 terminating at a distal end in a circular brush 34 preferably formed by twisting nylon bristles between strands of stainless steel wire 36. A suitable brush is made from type 304 stainless steel wire, 0.02 inches in diameter, mil spec MS209956, and type 612 natural level nylon, 0.005 inches in diameter, FDA# 21CFR1771-1500, and is available from Gordon Brush Company, Los Angeles, Ca. The initially straight brush is subsequently deformed into the generally circular illustrated configuration, with a stem portion 38 of the stainless steel wire 36 extending rearwardly through a central aperture of a circular sponge 40. A suitable sponge is a 2 inch diameter circle of 0.0625 inch thick open-cell cellulose sponge, #1935, with a 0.25 inch central hole, available from Lundell Manufacturing Corporation, Minneapolis, Mn. The circular brush 34 has a diameter of about 3.5 centimeters, while the surrounding sponge 40 has a diameter of about 5.0 centimeters. A typical cervix has a diameter of 5.0 to 5.5 centimeters. The stem portion 38 of the stainless steel wire 36 is press fit within a central bore 46 formed in a radially enlarged circular end flange 42 of a stem 44. The stem 44 is inserted through a sleeve 50 terminating in a second radially enlarged circular end flange 48. Accordingly, the end flange 42 forms an abutment surface for the rear face of the sponge 40 and serves to press the sponge 40 against the rear face of the circular brush 34. The flange 42 also serves as a stop restricting forward axial movement of sleeve 50 due to flange 42 having a greater outer diameter than the inner diameters of flange 48 and sleeve 50. The stem 44 terminates at an axially inward end in a semi-cylindrical connector tab end portion 52. A pin 54 extends transversely to the axis of the stem 44 from a central location on the flat interior surface of connector tab portion 52. A second sleeve 56 which includes a radially enlarged terminal circular flange 58 is dimensioned for a relatively tight fitting, sliding, frictional engagement over the stem 44 and also over a plunger shaft 64. As shown in FIG. 8, the plunger shaft 64 terminates in a second semi-cylindrical connector tab end portion 60 provided with a transversely extending aperture 62 dimensioned for frictional engagement with the pin 54 of tab end portion 52 of stem 44. Accordingly, it may now be understood that a selectively detachable connection is formed by stem 44 and plunger shaft 64, such that the stem 44 and attached brush 34 and sponge 40 may be removed as desired by sliding sleeve 56 rearwardly along shaft 64 until engaged tab end portions 52 and 60 are exposed. The pin 54 may then be manually disengaged from aperture 62, to complete detachment of stem 44 from shaft 64.

Plunger shaft 64 is formed by four axially extending ribs 66, 68, 70, and 72 disposed at ninety degree circumferential increments. A supporting cross formed by intersecting strut members 74, 76, 78, and 80, which form radially outwardly extending projections at a medial position of shaft 64, serves to maintain the plunger shaft 64 approximately centered within the barrel 12 in an assembled condition. The supporting cross cooperates, in the manner of a detent, with internal ridges 30 and 32 within barrel 12 (FIG. 8) to prevent inadvertent extension or retraction of the plunger assembly 33. A rear end portion of the plunger shaft 64 terminates in radially enlarged rib portions 82, 84, 86 and 88 integrally molded with a cylindrical end plug 90. An axially projecting gripping flange 92 extends transversely from an outer end face of plug 90 to provide a manual grasping surface to enable a user to extend, retract, and rotate the plunger assembly 33 relative to the barrel 12. The various components of the plunger assembly 33 are preferably formed from #PP14B12A co-polymer polypropylene, available from Branchcomb Industries, Sapulpa, Ok.

Figure 10:
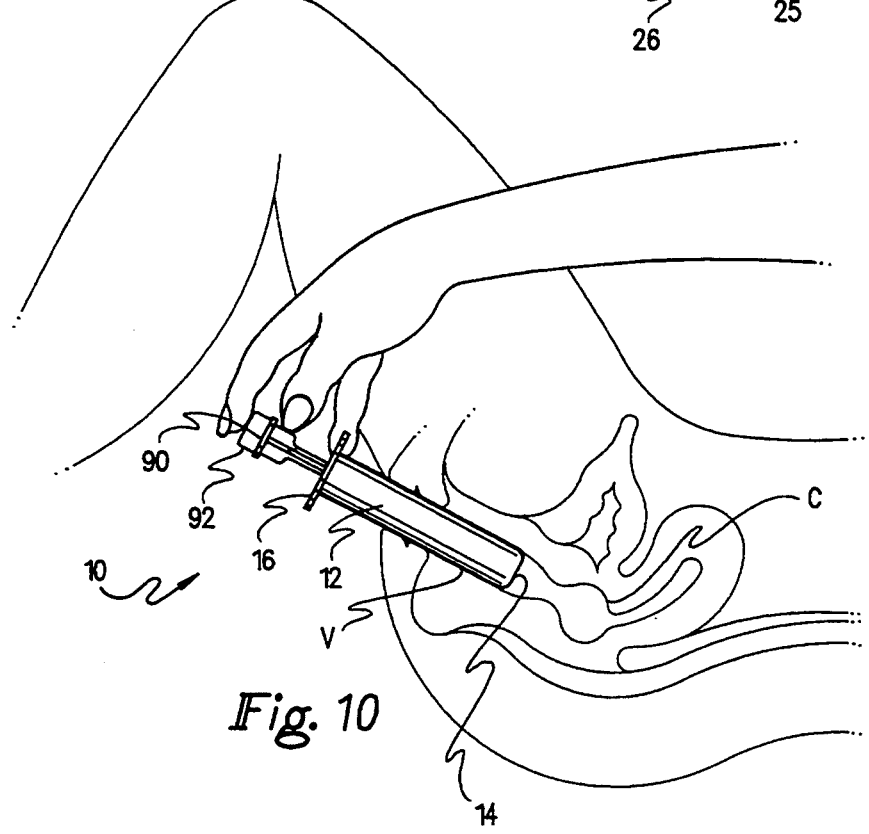
FIG. 10 is a diagrammatic view illustrating the manner of use of the cervical tissue sampling device of the present invention.

In the manner of use of the cervical tissue sampling device according to the present invention, a female lies in a generally reclined position as illustrated in FIG. 10 and inserts the barrel 12 into the vagina V. It should be noted that the barrel 12 of the cervical tissue sampling device 10 is shown in a partially inserted position in FIG. 10. In practice, the barrel is further inserted such that the circular open front end 14 of barrel 12 contacts the face of the cervix C, thereby allowing slight pressure to be applied to the face of the cervix C. In so doing, the os (or opening) of the cervix C is substantially axially aligned with the barrel 12 and when the plunger assembly 33 is extended, as described below, the bristles of the brush 34 are allowed to enter the os in order to obtain endocervical cells for analysis.

Figure 9:
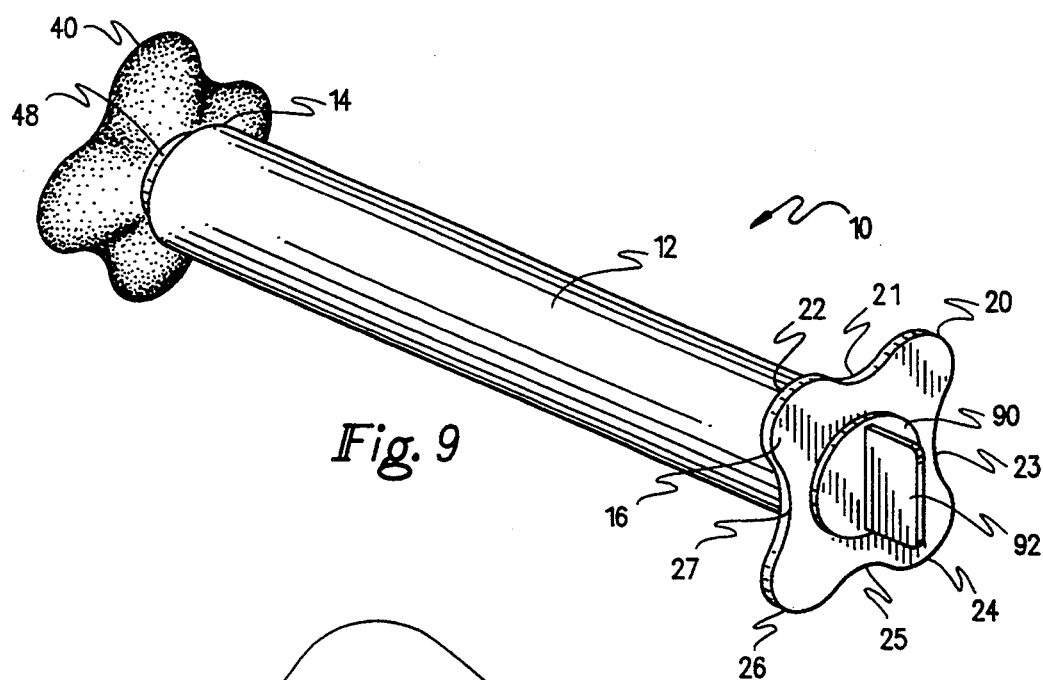
FIG. 9 is a rear perspective view illustrating the cervical tissue sampling device of the present invention in an extended condition.

With the plunger assembly 33 disposed in the retracted condition depicted in FIGS. 1 and 2, the supporting cross formed by struts 74, 76, 78, and 80 is disposed between ribs 30 and 32 (FIG. 8). In this condition, the circular sponge 40 is in a folded orientation within barrel 12, as shown in FIGS. 1, 2, 4, 6, and 7. The retracted condition of the sponge 40 is such that the sponge 40 is substantially located within the radial boundary of barrel 12 to facilitate insertion. After insertion of the barrel 12, the female extends the plunger assembly 33 with the aid of finger gripping flange 16, plug 90, and integral gripping flange 92. The extension of the plunger assembly 33 causes the supporting cross to snap past rib 32 (FIG. 8) due to the resilient nature of the plastic material forming struts 74, 76, 78, and 80. The plug 90 then is received in recess 29 (FIG. 2) in flange 16, limiting further extension of the plunger assembly 33. The recess 29 forms a journal bearing surface for rotationally mounting the plug 90 and attached plunger shaft 64 in an axially central orientation to facilitate sample collection. The sponge 40 then, due to its natural resiliency, springs to the open orientation shown in FIG. 9, exposing the circular brush 34 illustrated in FIG. 8. The exposed brush 34 and sponge 40 then collect endocervical, cervical cap, and vaginal wall tissue and mucous samples from the vagina V and cervix C, facilitated by manual rotation of the plunger assembly 33 by the user via gripping flange 92.

After sampling is complete, the female retracts the plunger assembly 33 to its starting position, aided by the tactile indication of retraction provided by the snapping of the support cross past rib 32, protecting the collected specimen on the brush 34 and sponge 40 within the barrel 12. The female then withdraws the device 10 by grasping flange 16, removes the plunger assembly 33 from the barrel 12, and detaches the axially outer end portion of the plunger assembly 33 including brush 34 and sponge 40, utilizing the detachable connection formed by connector tabs 52 and 60 shown in FIG. 8.

It should be noted that the sponge 40 not only functions as a specimen collection agent, but also as a cloak of protection for the brush 34 and the specimen sample thereon. As the plunger assembly 33 is being retracted, the sponge 40 folds back to its position shown in FIGS. 1 and 2, thereby encapsulating and protecting said brush and sample.

The sampling device 10 may be sold as a kit including a suitable lubricant gel to facilitate insertion, along with a small sealable container in which to mail or otherwise transmit detached outer end portion of the plunger assembly 33 including the sponge 40 and brush 34 to a laboratory for analysis.

The device 10 is extremely inexpensive and simple to use. Thus, the device may be utilized by women in the privacy of their own homes to collect tissue samples for analysis.

It is to be understood, however, that even though numerous characteristics and advantages of the present invention have been set forth in the foregoing description, together with details of the structure and function of the invention, the disclosure is illustrative only, and changes may be made in detail, especially in matters of materials, shape, size and arrangement of parts, within the principles of the invention to the full extent indicated by the broad general meaning of the terms in which the appended claims are expressed.

What is claimed is:

1. A cervical tissue sampling device, comprising:
   a barrel;
   a plunger disposed for reciprocal sliding movement in said barrel; and
   collecting means for collecting tissue secured to a distal end of said plunger; said collecting means including a brush and a sponge dimensioned and disposed to at least partially surround said brush when said plunger is retracted within said barrel.

2. The cervical tissue sampling device of claim 1, wherein said brush is circular.

3. The cervical tissue sampling device of claim 2, wherein said circular brush lies substantially in a plane substantially transverse to a longitudinal axis of said plunger.

4. The cervical tissue sampling device of claim 1, wherein said sponge is substantially circular.

5. The cervical tissue sampling device of claim 4, wherein said circular sponge, in an extended condition, lies substantially in a plane substantially transverse to a longitudinal axis of said plunger.

6. The cervical tissue sampling device of claim 1, wherein said brush is disposed adjacent to and axially outwardly of said sponge.

7. The cervical tissue sampling device of claim 1, further comprising connection means detachably securing said collecting means to said plunger.

8. The cervical tissue sampling device of claim 7, wherein said connection means comprises selectively interlocking first and second tab portions.

9. The cervical tissue sampling device of claim 8, wherein said first and second tab portions are each semi-cylindrical.

10. The cervical tissue sampling device of claim 9, wherein said first tab portion includes a transverse pin and said second tab portion includes a mating transverse aperture.

11. The cervical tissue sampling device of claim 1, further comprising detent means to substantially prevent inadvertent extension or retraction of said plunger relative to said barrel and to provide a tactile indication to a user of plunger retraction.

12. The cervical tissue sampling device of claim 11, wherein said detent means comprises at least one axially spaced internal ridge in said barrel dimensioned for engagement with at least one radially outwardly extending projection on said plunger.

13. The cervical tissue sampling device of claim 1, further comprising bearing means for mounting said plunger in an extended condition for substantially central rotation within said barrel.

14. The cervical tissue sampling device of claim 13, wherein said bearing means comprises a plug on said plunger and a complementary recess formed adjacent a proximal end of said barrel, said recess dimensioned and disposed for at least partially receiving said plug in said extended condition of said plunger.

15. The cervical tissue sampling device of claim 14, wherein said recess is disposed in a finger grip flange formed adjacent said proximal end of said barrel.

16. A cervical tissue sampling device, comprising:
    a barrel;
    a plunger disposed for reciprocal sliding movement in said barrel;
    at least one radially outwardly extending projection on said plunger;
    at least one internal ridge in said barrel dimensioned and disposed for engagement with said projection on said plunger to substantially prevent inadvertent extension or retraction of said plunger relative to said barrel and to provide a tactile indication to a user of plunger retraction; and
    a collecting member for collecting tissue secured to a distal end of said plunger.

17. The cervical tissue sampling device of claim 16, wherein said at least one internal ridge comprises a pair of axially spaced internal ridges.

18. The cervical tissue sampling device of claim 16, further comprising a bearing mounting said plunger in an extended condition for substantially central rotation within said barrel.

19. The cervical tissue sampling device of claim 18, wherein said bearing comprises a plug on said plunger and a complementary recess formed adjacent a proximal end of said barrel, said recess dimensioned and disposed for at least partially receiving said plug in an extended condition of said plunger.

20. The cervical tissue sampling device of claim 19, wherein said recess is disposed in a finger grip flange formed adjacent said proximal end of said barrel.

21. The cervical tissue sampling device of claim 16, wherein said collecting member comprises a brush.

22. The cervical tissue sampling device of claim 21, wherein said brush is substantially circular.

23. The cervical tissue sampling device of claim 16, wherein said collecting member comprises a thin, flexible sponge.

24. The cervical tissue sampling device of claim 23, wherein said sponge is substantially circular.

25. The cervical tissue sampling device of claim 23, wherein said sponge, in an extended condition, lies substantially in a plane substantially transverse to a longitudinal axis of said plunger.

26. The cervical tissue sampling device of claim 16, wherein said collecting member comprises a brush and a thin, flexible sponge.

27. The cervical tissue sampling device of claim 26, wherein said brush is substantially circular.

28. The cervical tissue sampling device of claim 27, wherein said substantially circular brush lies substantially in a plane substantially transverse to a longitudinal axis of said plunger.

29. The cervical tissue sampling device of claim 26, wherein said sponge is substantially circular.

30. The cervical tissue sampling device of claim 26, wherein said sponge, in an extended condition, lies substantially in a plane substantially transverse to a longitudinal axis of said plunger.

31. The cervical tissue sampling device of claim 26, wherein said sponge is dimensioned and disposed to at least partially surround said brush when said plunger is retracted within said barrel.

32. The cervical tissue sampling device of claim 26, wherein said brush is disposed adjacent to and axially outwardly of said sponge.

33. The cervical tissue sampling device of claim 16, further comprising a connector detachably securing said collecting member to said plunger.

34. The cervical tissue sampling device of claim 33, wherein said connector comprises selectively interlocking first and second tab portions.

35. The cervical tissue sampling device of claim 34, wherein said first tab portion includes a transverse pin and said second tab portion includes a mating transverse aperture.

36. A cervical tissue sampling device, comprising:
a barrel;
a plunger disposed for reciprocal sliding movement in said barrel;
a thin, flexible, sponge secured adjacent a distal end of said plunger, said sponge, in an extended condition of said plunger substantially disposed in a plane substantially transverse to a longitudinal axis of said plunger;
a brush secured to said plunger axially outwardly of said sponge; and
said sponge dimensioned and disposed to at least partially surround said brush when said plunger is retracted within said barrel.

37. cervical tissue sampling device, comprising:
a barrel;
a plunger disposed for reciprocal sliding movement in said barrel;
a collecting member;
a connector detachably securing said collecting member to said plunger, said connector comprising a first tab portion including a substantially transverse pin and a second tab portion including a mating substantially transverse aperture, and a sleeve dimensioned for selective frictional engagement over said first and second tab portions to selectively secure said collecting member to said plunger.

38. The cervical tissue sampling device of claim 37, wherein said first and second tab portions are each substantially semicylindrical and include abutting flat interior surfaces.

39. A cervical tissue sampling device, comprising:
a barrel;
a plunger disposed for reciprocal sliding movement in said barrel;
a collecting member for collecting tissue secured to a distal end of said plunger;
a bearing mounting said plunger in an extended condition for substantially central rotation in said barrel, said bearing including a plug on said plunger and a complementary recess formed adjacent a proximal end of said barrel, said recess dimensioned and disposed for at least partially receiving said plug in an extended condition of said plunger.

40. The cervical tissue sampling device of claim 39, wherein said recess is disposed in a finger grip flange formed adjacent said proximal end of said barrel.

* * * * *